US011707203B2

(12) United States Patent
Deitz

(10) Patent No.: US 11,707,203 B2
(45) Date of Patent: Jul. 25, 2023

(54) SYSTEMS FOR GENERATING IMAGE-BASED MEASUREMENTS DURING DIAGNOSIS

(71) Applicant: WENZEL SPINE, INC., Austin, TX (US)

(72) Inventor: Adam Deitz, Austin, TX (US)

(73) Assignee: WENZEL SPINE, INC., Austin, TX (US)

(*) Notice: Subject to any disclaimer, the term of this patent is extended or adjusted under 35 U.S.C. 154(b) by 793 days.

(21) Appl. No.: 15/728,854

(22) Filed: Oct. 10, 2017

(65) Prior Publication Data

US 2018/0098715 A1    Apr. 12, 2018

Related U.S. Application Data

(60) Provisional application No. 62/424,690, filed on Nov. 21, 2016, provisional application No. 62/406,703, filed on Oct. 11, 2016.

(51) Int. Cl.
*A61B 5/055* (2006.01)
*A61B 5/00* (2006.01)
(Continued)

(52) U.S. Cl.
CPC ............ *A61B 5/055* (2013.01); *A61B 5/1071* (2013.01); *A61B 5/1079* (2013.01);
(Continued)

(58) Field of Classification Search
CPC .... A61B 2090/3966; A61B 2090/3983; A61B 34/10; A61B 5/0555; A61B 5/1071; A61B 5/1077; A61B 5/1079; A61B 5/4561
See application file for complete search history.

(56) References Cited

U.S. PATENT DOCUMENTS 3,941,127 A    3/1976 Froning
4,743,256 A    5/1988 Brantigan
(Continued)

FOREIGN PATENT DOCUMENTS

EP    0260044 A1    3/1988
EP    0176728 B1    7/1989
(Continued)

OTHER PUBLICATIONS

Bostman et al., Posterior Spinal Fusion Using Internal Fixation with the Daab Plate, ACTA ortho Scan 55:310-314 (1984).

*Primary Examiner* — Yi-Shan Yang
*Assistant Examiner* — Alexei Bykhovski
(74) *Attorney, Agent, or Firm* — Buchalter; Cecily Anne O'Regan

(57) ABSTRACT

Devices, systems, tools and methods are disclosed during diagnosis and treatment of spinal conditions. A cervical plumb line device is disclosed which can be used to produce a measurement of the sagittal vertical axis associated with a target part of a patient's cervical spinal anatomy from two or more radiographic images. Also disclosed is an apparatus for measuring the angulation of a patient's spinal anatomy relative to a cervical plumb line which uses a plurality of bolsters. A device that can be used to assist in implantation of an interbody device during spinal fusion device is also disclosed. Systems which produce geometric data describing optimized spinal fusion geometric at a spine level selected to receive spinal fusion.

8 Claims, 12 Drawing Sheets

(51) Int. Cl.
*A61B 34/10* (2016.01)
*A61B 5/107* (2006.01)
*A61B 90/00* (2016.01)

(52) U.S. Cl.
CPC ............ *A61B 5/4561* (2013.01); *A61B 34/10* (2016.02); *A61B 5/1077* (2013.01); *A61B 2090/3966* (2016.02); *A61B 2090/3983* (2016.02)

(56) References Cited

U.S. PATENT DOCUMENTS

| | | |
|---|---|---|
| 5,349,956 A | 9/1994 | Bonutti |
| 5,427,116 A | 6/1995 | Noone |
| 6,560,476 B1 | 5/2003 | Pelletier et al. |
| 6,662,148 B1 | 12/2003 | Adler et al. |
| 7,502,641 B2 | 3/2009 | Breen |
| 7,935,133 B2 | 5/2011 | Malek |
| 7,955,133 B2 | 6/2011 | Scheele et al. |
| 8,014,575 B2 * | 9/2011 | Weiss .................. A61B 5/0042 382/128 |
| 8,043,337 B2 | 10/2011 | Klyce et al. |
| 8,048,120 B1 | 11/2011 | Fallin et al. |
| 8,070,817 B2 | 12/2011 | Gradl et al. |
| 8,114,132 B2 | 2/2012 | Lyons et al. |
| 8,128,659 B2 | 3/2012 | Ginsberg et al. |
| 8,157,842 B2 | 4/2012 | Phan et al. |
| 8,660,329 B2 | 2/2014 | Skalli et al. |
| 8,676,293 B2 | 3/2014 | Breen et al. |
| 8,777,878 B2 | 7/2014 | Deitz |
| 9,138,163 B2 | 9/2015 | Deitz |
| 9,277,879 B2 | 3/2016 | Deitz |
| 9,510,771 B1 | 12/2016 | Finley et al. |
| 9,795,451 B2 | 10/2017 | Gorek et al. |
| 10,959,786 B2 | 3/2021 | Deitz |
| 2002/0077543 A1 | 6/2002 | Grzeszczuk et al. |
| 2005/0245817 A1 | 11/2005 | Clayton et al. |
| 2007/0219445 A1 | 9/2007 | Liebschner et al. |
| 2007/0276296 A1 * | 11/2007 | Bright .................. A61B 5/1071 600/595 |
| 2008/0039866 A1 | 2/2008 | Stetz et al. |
| 2008/0114267 A1 | 5/2008 | Lloyd et al. |
| 2008/0300605 A1 | 12/2008 | Rinner |
| 2009/0024164 A1 | 1/2009 | Neubardt |
| 2009/0297012 A1 * | 12/2009 | Brett .................. G06V 20/695 382/128 |
| 2010/0030232 A1 | 2/2010 | Zehavi et al. |
| 2010/0086185 A1 | 4/2010 | Weiss |
| 2011/0029020 A1 | 2/2011 | Gordon et al. |
| 2011/0054531 A1 | 3/2011 | Lamborne et al. |
| 2011/0066186 A1 | 3/2011 | Boyer et al. |
| 2011/0071437 A1 * | 3/2011 | Merchant .............. G01B 3/563 600/587 |
| 2011/0092859 A1 | 4/2011 | Neubardt |
| 2011/0144692 A1 | 6/2011 | Saladin et al. |
| 2011/0166600 A1 | 7/2011 | Lamborne et al. |
| 2011/0224731 A1 | 9/2011 | Smisson, III et al. |
| 2011/0224740 A1 | 9/2011 | Smisson, III et al. |
| 2011/0286630 A1 | 11/2011 | Harder et al. |
| 2011/0296630 A1 | 12/2011 | Frazer et al. |
| 2011/0313458 A1 | 12/2011 | Butler et al. |
| 2011/0319936 A1 | 12/2011 | Gordon et al. |
| 2011/0319941 A1 | 12/2011 | Bar et al. |
| 2012/0010662 A1 | 1/2012 | O'Neil et al. |
| 2012/0016418 A1 | 1/2012 | Chin et al. |
| 2012/0078304 A1 | 3/2012 | Jensen et al. |
| 2012/0078305 A1 | 3/2012 | Wang et al. |
| 2012/0083844 A1 | 4/2012 | Linares |
| 2012/0083846 A1 | 4/2012 | Wallenstein et al. |
| 2012/0089184 A1 | 4/2012 | Yeh |
| 2012/0095512 A1 | 4/2012 | Nihalani |
| 2012/0101528 A1 | 4/2012 | Souza et al. |
| 2012/0109198 A1 | 5/2012 | Dryer et al. |
| 2012/0109203 A1 | 5/2012 | Dryer et al. |
| 2012/0109205 A1 | 5/2012 | Mitchell et al. |
| 2012/0123475 A1 | 5/2012 | Ahn et al. |
| 2012/0130285 A1 | 5/2012 | Deitz |
| 2012/0136390 A1 | 5/2012 | Butler et al. |
| 2012/0143252 A1 | 6/2012 | Robinson |
| 2012/0150228 A1 | 6/2012 | Zappacosta et al. |
| 2012/0158061 A1 | 6/2012 | Koch et al. |
| 2012/0158063 A1 | 6/2012 | Altarac et al. |
| 2012/0172700 A1 | 7/2012 | Krishnan et al. |
| 2012/0310292 A1 | 12/2012 | Smisson, III et al. |
| 2013/0131486 A1 * | 5/2013 | Copf .................. A61F 2/30942 600/407 |
| 2014/0003684 A1 | 1/2014 | Ayed et al. |
| 2014/0108983 A1 | 4/2014 | William R. et al. |
| 2014/0323845 A1 | 10/2014 | Forsberg |
| 2015/0182288 A1 | 7/2015 | Greenwald et al. |
| 2016/0210374 A1 | 7/2016 | Mosnier et al. |
| 2016/0213443 A1 | 7/2016 | Lueck et al. |
| 2016/0235479 A1 | 8/2016 | Mosnier et al. |
| 2018/0061048 A1 | 3/2018 | Weiss |
| 2020/0085507 A1 | 3/2020 | Deitz |
| 2021/0220057 A1 | 7/2021 | Deitz |

FOREIGN PATENT DOCUMENTS

| | | |
|---|---|---|
| WO | 9810722 A1 | 3/1998 |
| WO | 0012033 A1 | 3/2000 |
| WO | 2013158960 A1 | 10/2013 |
| WO | 2015040552 A1 | 3/2015 |
| WO | 2015056131 A1 | 4/2015 |
| WO | 2016196566 A3 | 12/2016 |
| WO | 2018071496 A2 | 4/2018 |
| WO | 2018071496 A3 | 4/2018 |

* cited by examiner

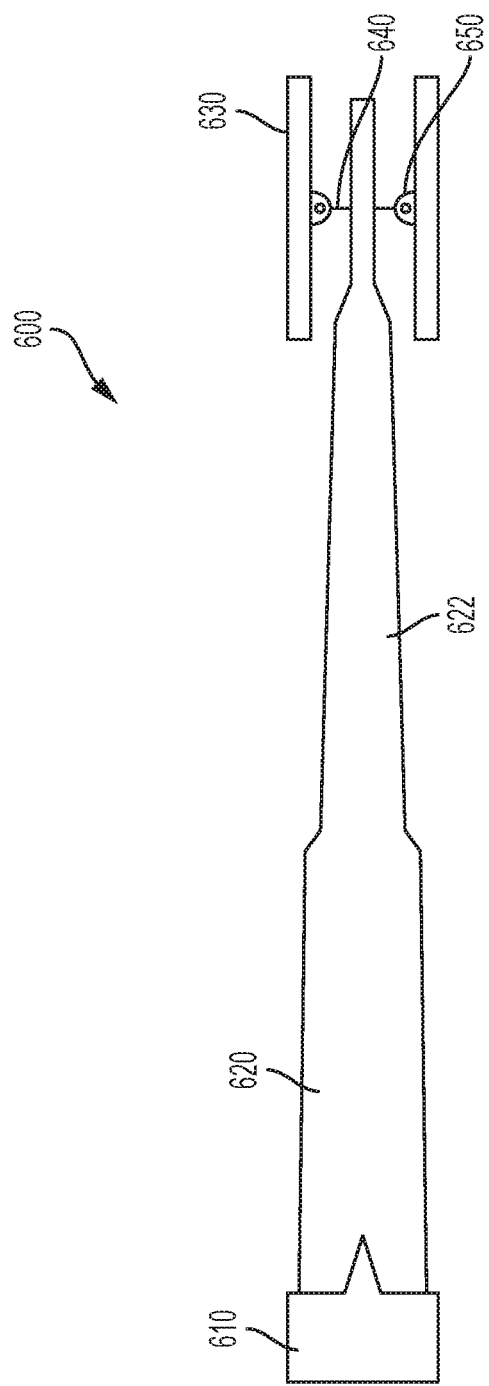

SYSTEMS FOR GENERATING IMAGE-BASED MEASUREMENTS DURING DIAGNOSIS

CROSS-REFERENCE

This application claims the benefit of U.S. Provisional Application No. 62/406,703 filed Oct. 11, 2016, entitled Apparatus and Methods for Generating Image Based Measurements During Diagnosis and 62/424,690 filed Nov. 21, 2016, entitled Apparatus and Methods for Generating Image Based Measurements During Diagnosis which applications are incorporated herein by reference.

BACKGROUND

Posterior fusion with traditional impacted devices often requires stretching of the posterior longitudinal ligaments (PLL) to accommodate the height of the implant that is being inserted between vertebral bodies of the spine. When the interbody anterior height is within a known safe range (e.g., less than or equal to $PDH_{max}$) then PLL distraction is avoided. In contrast, where the interbody anterior height between adjacent vertebral bodies is uncertain or greater than $PDH_{max}$, then PLL distraction may be required. For 58% of the degenerative fusion patient population, posterior access to the spine requires exceeding the known safe rage of the PLL, thus requiring distraction. These patients would benefit from lateral or oblique surgery because PLL stretching could be avoided.

Point loading and compromised arthrodesis may occur when the interbody and endplates of the vertebral bodies are not flush. Point loading, and potential subsistence can be avoided by keeping the interbody posterior height above the known safe rage of the facets. This can also maximize ingrowth surface area and assure the best contact of the graft endplates.

The anterior longitudinal ligament (ALL) may need to be stretched or released during spinal fusion procedures depending on the anterior height of the interbody device. ALL stretching is avoided when the anterior height of the interbody device is less than the known safe range of the ALL (e.g., less than the $ADH_{max}$). In contrast, where the interbody anterior height between adjacent vertebral bodies is uncertain or greater than $ADH_{max}$, then the ALL may need to be stretched or released.

A need exists to be able to acquire image-derived measurements of sagittal alignment, in particular various plumb line measurements referred to as Sagittal Vertical Axis (SVA), from a fluoroscope. Usually, these measurements are acquired via standing full-spine length x-ray images of the patient in a standing weight bearing un-assisted posture. To calculate SVA for cervical vertebral bodies, it is necessary to have images that contain both the sacrum up to C0.

However, if these measurements are to be taken from a fluoroscope, there are operating restrictions—namely the reduced height that the image intensifier can rise to a C-arm is parallel to the floor. Lateral view images of the cervical spine cannot therefore be taken because the C-arm cannot go height enough. What is needed is a fiducial and patient-mounting device aspect, a plumb line device aspect, and a connecting arm scaling object aspect and methods. Also what is needed are systems that produce geometric data describing optimized spinal fusion geometry for a spine level selected to receive spinal fusion. What is also needed are systems and methods for measuring angulation of spinal anatomy relative to a plumb line. Additionally, trial instruments for use in applying force to distraction plates which are applied against vertebral end plates are also needed. Additionally, systems and methods for producing optimized spinal fusion geometric configurations and recommendations for interventions are also needed.

SUMMARY

Disclosed are devices, systems, tools and methods for generating image-based measurements which can be used during diagnosis. A cervical plumb line device is disclosed which can be used to produce a measurement of the sagittal vertical axis associated with a target part of a patient's cervical spinal anatomy from two or more radiographic images. Also disclosed is an apparatus for measuring the angulation of a patient's spinal anatomy relative to a cervical plumb line which uses a plurality of bolsters. A device that can be used to assist in implantation of an interbody device during spinal fusion device is also disclosed. Systems which produce geometric data describing optimized spinal fusion geometry at a spine level selected to receive spinal fusion.

An aspect of the disclosure is directed to orthopedic plumb line devices. Suitable orthopedic plumb line devices comprise: an elongated first radiopaque arm having a first arm end and a second arm end wherein the first arm end is configurable to engage a surface of a patient, a variable length second radiopaque arm which rotatably extends from the first radiopaque arm; a third radiopaque arm having a connection end and a patient contact end connected to the first radiopaque arm at the connection end at a connection position along a length of the first radiopaque arm Plumb line devices can also include, for example, reference markings along a portion of a length of the second radiopaque arm. The reference markings can denote a linear distance from the elongated first radiopaque arm. Additionally, the second radiopaque arm can be detachable and/or extendable. Additionally, in some configurations, the second radiopaque arm can have a weighted end.

Another aspect of the disclosure is directed to methods of imaging a patient. Suitable methods comprise: positioning an orthopedic plumb line device adjacent a surface of a patient wherein the orthopedic plumb line device comprises an elongated first radiopaque arm having a first arm end and a second arm end wherein the first arm end is configurable to engage a surface of a patient, a variable length second radiopaque arm which rotatably extends from the first radiopaque arm, a third radiopaque arm having a connection end and a patient contact end connected to the first radiopaque arm at the connection end at a connection position along a length of the first radiopaque arm, taking a first radiographic image of the patient wherein the first radiographic image includes a portion of a first target spinal anatomy of the patient and a portion of the orthopedic plumb line; taking a second radiographic image of the patient while the patient is sitting wherein the second radiographic image includes a portion of a second target spinal anatomy of the patient and a portion of the orthopedic plumb line, and comparing the first radiographic image and the second radiographic image; and generating a measurement of a sagittal vertical axis between the first and second target spinal anatomy components. Additionally, the method can include the step of extending the second radiopaque arm.

Still another aspect of the disclosure is directed to systems for measuring an angulation of a spinal anatomy of a patient relative to an orthopedic plumb line. Suitable systems comprise: a patient bolstering system having multiple bolsters which engages the patient dorsally at lumbar spine, and ventrally across the hips and above the knees which allows the patient to achieve a range of pelvic tilt angles; and a processing system to measure a plurality of angles selected from angles between anatomic components, angles between one or more anatomic components and a direction of gravity, and a pelvic tilt angle. Additionally, an orthopedic plumb line device can be included in the system. The orthopedic plumb line can allow for a plumb line radiographic marker to be visible in images taken of the spine, pelvis, and/or extremities, and comprise an elongated first radiopaque arm having a first arm end and a second arm end wherein the first arm end is configurable to engage a surface of a patient, a variable length second radiopaque arm which rotatably extends from the first radiopaque arm, a third radiopaque arm having a connection end and a patient contact end connected to the first radiopaque arm at the connection end at a connection position along a length of the first radiopaque arm. The plumb line can also be a simple radiographic marker.

Yet another aspect of the disclosure is directed to methods of measuring angulation of a spinal anatomy relative to a plumb line. Suitable methods comprise: engaging a patient bolstering system having multiple bolsters configured to engage the patient dorsally at lumbar spine, and ventrally across the hips and above the knees, positioning the patient at a first position, taking a first radiographic image of the patient wherein the first radiographic image includes a portion of a target spinal anatomy of the patient and a portion of the orthopedic plumb line; taking a second radiographic image of the patient wherein the second radiographic image includes a portion of a target spinal anatomy of the patient and a portion of the orthopedic plumb line; comparing the first radiographic image and the second radiographic image; and generating a measurement based on the comparison of the first radiographic image and the second radiographic image. The methods can also comprise one or more of each of moving the patient through a range of pelvic tilt angles and taking a radiographic image at each new position, projecting a post-operative pelvic tilt angle from a projected post-operative angulation from a plurality of angles selected from angles between anatomic components, angles between one or more anatomic components and a direction of gravity, and a pelvic tilt angle; determining a direction of gravity within the radiographic images; and generating radiographic images that are automatically aligned towards a selected direction of gravity.

Another aspect of the disclosure is directed to trial instruments for orthopedic surgery. Suitable trial instruments comprise: an elongated member; a rotatable knob at a proximal end of the elongated member; and a pair of distraction plates at a distal end of the elongated member wherein a position or distraction force of the distraction plates is controllable by the rotatable knob. In at least some configurations, the trial instruments can further comprise reference markings about the elongated member adjacent the rotatable knob. Additionally, the pair of distraction plates can have a flat surface. The distraction plates can be parallel to each other when the distraction plates are extended away from the elongated member, and/or when the distraction plates are in a low-profile pre-deployment configuration. A force application feedback mechanism can also be provided. A rotatable knob can be used to apply force to the distraction plates. Additionally, the distraction plates can be connected to the elongated shaft via a connector with a rotation point.

Still another aspect of the disclosure is directed to methods of using a trial instrument for orthopedic surgery. Suitable methods comprise: inserting the trial instrument between an endplate of a first vertebral body and an endplate of a second vertebral body adjacent the first vertebral body, the trial instrument comprising an elongated member, a rotatable knob at a proximal end of the elongated member, and a pair of distraction plates at a distal end of the elongated member wherein a position of the distraction plates is controllable by the rotatable knob, adjusting a distance between the pair of distraction plates; increasing a space between adjacent distraction plates. The trial instrument can further comprise reference markings about the elongated member adjacent the rotatable knob. Additionally, the pair of distraction plates can have a flat surface. The method can include extending the distraction plates away from the elongated member, and/or providing feedback to a user of the amount of force applied to the distraction plates. The extraction plates can be rotated about a connection point during at least some methods.

Another aspect of the disclosure is directed to systems for producing geometric data describing an optimized spinal fusion geometric configuration at a spine level selected to receive spinal fusion, for use during spine surgery or during pre-operative planning. Suitable systems comprise a processor wherein the processor is configured to: (a) receive one or more images of a spine wherein the one or more images includes a cervical plumb line device; (b) process the received images to derive measurements of one or more of a spinal alignment and a range of motion at a spine level selected to receive spinal fusion surgery; and (c) utilize the derived measurements to calculate an optimized spinal fusion geometric configuration for a target spine level. Additionally, the processor can perform one or more of each of the following steps: receiving configuration parameters from a user; and analyzing the calculated geometric configuration and recommending a surgical approach; receiving and processing one or more of non-image patient data and additional images.

Yet another aspect of the disclosure is directed to systems for producing patient specific recommendations for intervention. Suitable systems comprise a processor configured to: (a) process image-derived measurement data of at least one of spinal alignment, range of motion at target spine levels adjacent to a spinal fusion spine level measured across one or more spinal radiographic images; (b) utilize image-derived measurement data to calculate a measurement of a risk of adjacent level disease, and (c) select an intervention from a list of interventions based on the calculated measurement of risk. The list of interventions can further be delimited to, for example, include one or more patient self-directed interventions, include interventions generated via a set of user configured variables that do not vary from patient to patient, include interventions selected based on a rationale of avoiding or delaying a progressions of adjacent level disease, and include one or more of: activity reduction, modification or substitution; weight loss, physical therapy focused on core/neck strength, physical therapy focused on addressing pelvic anteversion or retroversion; and interventions to address functional anomalies at adjacent levels. Additionally, the data received may be either at a single time point or may include multiple time points, and in the case of multiple time points the image-derived measurements are further delimited to include an analysis of the difference in measurements as taken between two or more time points.

INCORPORATION BY REFERENCE

All publications, patents, and patent applications mentioned in this specification are herein incorporated by reference to the same extent as if each individual publication, patent, or patent application was specifically and individually indicated to be incorporated by reference. References include:

U.S. Pat. No. 7,502,641 B2 issued Mar. 10, 2009 to Breen for Method for imaging the relative motion of skeletal segments;

U.S. Pat. No. 8,676,293 B2 issued Mar. 18, 2014 to Breen et al. for Devices, systems and methods for measuring and evaluating the motion and function of joint structures and associated muscles, determining suitability for orthopedic intervention, and evaluating efficacy of orthopedic intervention;

U.S. Pat. No. 8,777,878 B2 issued Jul. 15, 2014, to Deitz for Devices, systems and methods for measuring and evaluating the motion and function of joints and associated muscles;

U.S. Pat. No. 9,138,163 B2 issued Sep. 22, 2015 to Deitz for Systems and devices for an integrated imaging system with real-time feedback loop and methods therefor; and U.S. Pat. No. 9,277,879 B2 issued Mar. 8, 2016 to Deitz for Systems and devices for an integrated imaging system with real-time feedback loops and methods therefor;

US 2016/0235479 A1 published Aug. 18, 2016 to Mosnier et al., for Method making it possible to produce the ideal curvature of a rod of vertebral osteosynthesis material designed to support a patient vertebral column;

US 2016/0210374 A1 published Jul. 21, 2016 to Mosnier, et al. for Method making it possible to produce the ideal curvature of a rod of vertebral osteosynthesis material designed to support a patient's vertebral column;

WO2015/040552 A1 published Mar. 26, 2015 to Mosnier et al. for Method making it possible to produce the ideal curvature of a rod of vertebral osteosynthesis material designed to support a patient vertebral column; and WO2015/056131 A1 published Apr. 23, 2015 to Mosnier et al. for Method making it possible to produce the ideal curvature of a rod of vertebral osteosynthesis material designed to support a patient's vertebral column.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

FIG. 6 illustrates a trial instrument;

DETAILED DESCRIPTION

Acronyms

Figure 1A:
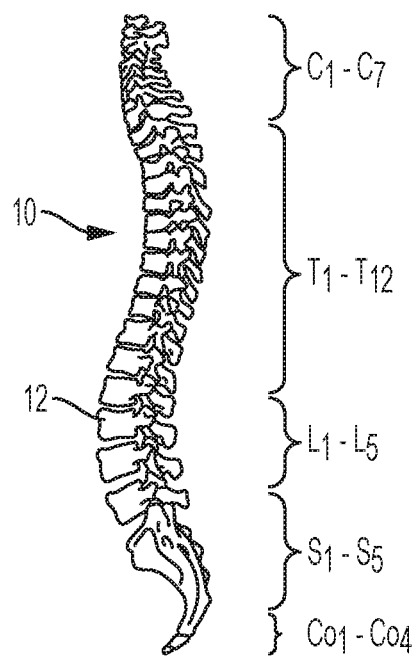
FIG. 1A is a lateral view of a normal human spinal column.

ADH—Anterior (vertebral) Disc Height
ALD—Adjacent Level Disease
ALL—Anterior Longitudinal Ligaments
API—Application Program Interface
CPU—Computer Processing Unit
LL—Lumbar Lordosis
MID—Millimeters of Direct Compression
MLO—Millimeters of Listhetic Offset
PDA—Personal Digital Assistant
PDH—Posterior (vertebral) Disc Height
PI—Pelvic Incidence
PLL—Posterior Longitudinal Ligaments
RAM—Random Access Memory
ROM—Read Only Memory
SMS—Short Message Service
SVA—Sagittal Vertical Axis
TCA—Target Construct Achievable Anatomical Background FIG. 1A illustrates the human spinal column 10 which is comprised of a series of thirty-three stacked vertebrae 12 divided into five regions. The cervical region includes seven vertebrae, known as C1-C7. The thoracic region includes twelve vertebrae, known as T1-T12. The lumbar region contains five vertebrae, known as L1-L5. The sacral region is comprised of five fused vertebrae, known as S1-S5, while the coccygeal region contains four fused vertebrae, known as Co1-Co4. The spine has regions that have an inward curvature (lordosis), e.g., the lumbar and cervical regions, and an outward (convex) curvature (kyphosis), e.g., in the thoracic and sacral regions.

Figure 1B:
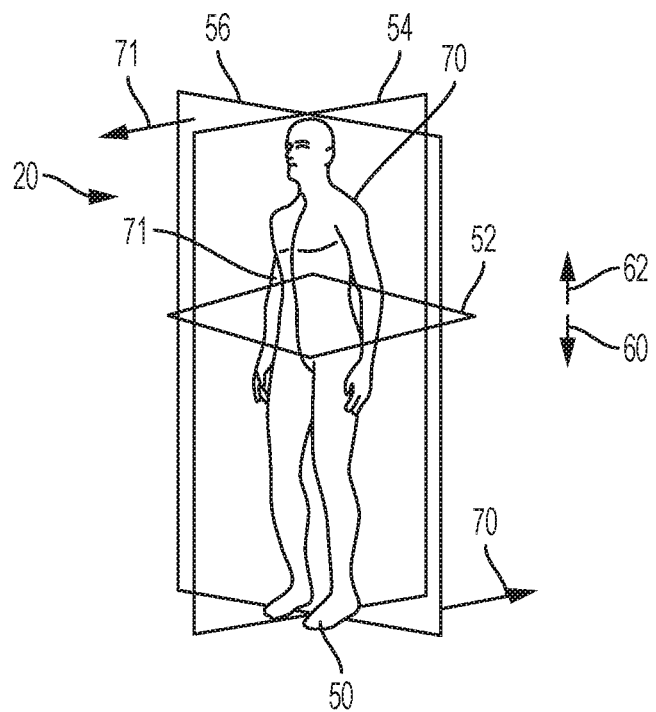
FIG. 1B illustrates a human body with the planes of the body identified.

In order to understand the configurability, adaptability, and operational aspects of the invention disclosed herein, it is helpful to understand the anatomical references of the body 50 with respect to which the position and operation of the devices, and components thereof, are described. FIG. 1B illustrates an overview of a patient 20 of three anatomical planes generally used in anatomy to describe the human body and structure within the human body. The three anatomical planes are: the axial plane 52, the sagittal plane 54 and the coronal plane 56. Additionally, devices and the operation of devices and tools may be better understood with respect to the caudad 60 direction and/or the cephalad direction 62. Devices and tools can be positioned dorsally 70 (or posteriorly) such that the placement or operation of the device is toward the back or rear of the body. Alternatively, devices can be positioned ventrally 71 (or anteriorly) such that the placement or operation of the device is toward the front of the body. Various embodiments of the devices, systems and tools of the present invention may be configurable and variable with respect to a single anatomical plane or with respect to two or more anatomical planes. For example, a subject or a feature of the device may be described as lying within and having adaptability or operability in relation to a single plane. A device may be positioned in a desired location relative to a sagittal plane and may be moveable between a number of adaptable positions or within a range of positions.

A variety of users can use the devices, systems and methods described herein. To distinguish between pre-operative, operative, and post-operative use or application, surgical user has been used. However, as will be appreciated by those skilled in the art, the surgical user can be the surgeon or anyone who assists the surgeon during the surgical process at any time in the work flow, and should not be considered limiting.

Cervical Plumb Line Devices

Figure 2B:
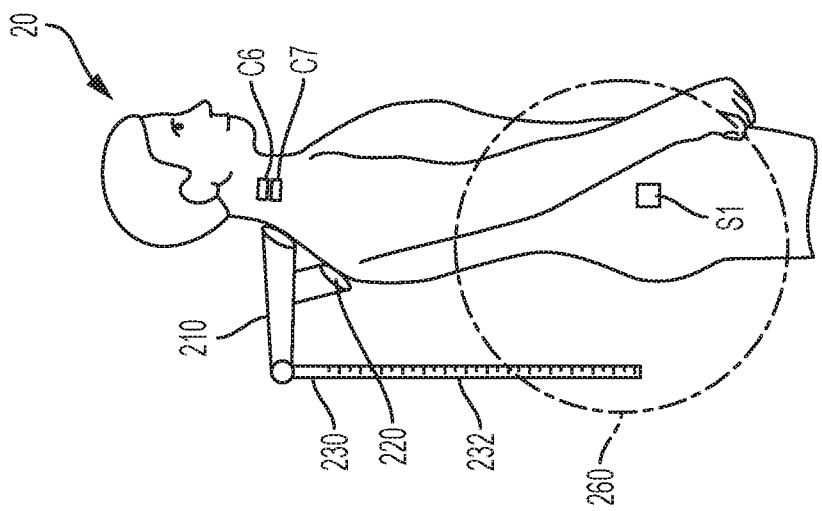
FIGS. 2A-B illustrate a seated view of a patient with cervical anatomy and standing view of a patient with sacral anatomy with a cervical plumb line device associated with the patient.
Figure 2A:
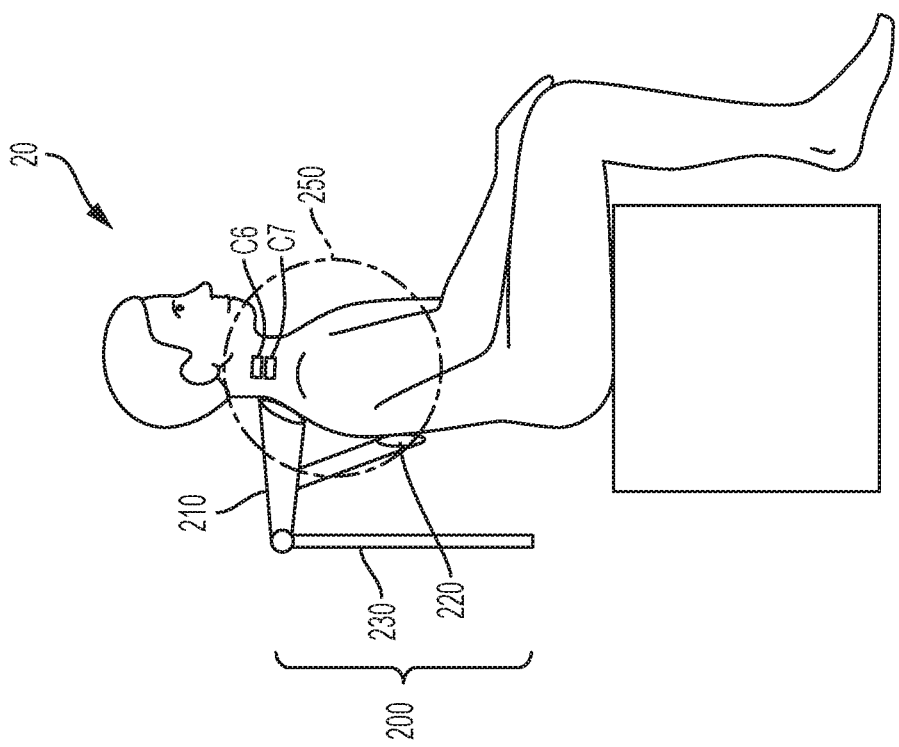

FIGS. 2A-B illustrate a seated view of a patient 20 with portions of the cervical anatomy (specifically vertebral bodies C6 and C7 of the spine) within an imaging field of view 250. A cervical plumb line device is 200 shown at least partially within the imaging field of view 250 and engaging an exterior dorsal surface of the patient 20 approximately at the vertebral bodies C6 and C7. The fiducial plumb line device 200 has a first radiopaque arm 210 that extends substantially perpendicularly from a dorsal surface of the patient. A second radiopaque arm 220 engages the first radiopaque arm 210 along its length and is angled towards the dorsal surface of the patient 20 below the position where the second radiopaque arm 220 engages the dorsal surface of the patient 20. A third radiopaque arm 230 is connected to the first radiopaque arm 210 at an end opposite the end where the first radiopaque arm 210 engages the patient 20. The third radiopaque arm 230 is retractable, thus allowing it to achieve varying lengths in use. Turning to FIG. 2B, a standing view of a patient 20 with sacral anatomy illustrated is provided. In addition to showing the C6 and C7 vertebra, the S1 vertebra is also illustrated. The cervical plumb line device illustrated in FIG. 2A is also shown associated with the patient. In this configuration, because the patient is standing the third radiopaque arm 230 is extended. Additionally, reference markings 232 can be provided on the third radiopaque arm which provide size information in the resulting images. The size of the field need not change between the views of FIG. 2A and FIG. 2B, and will typically be the same.

Figure 3B:
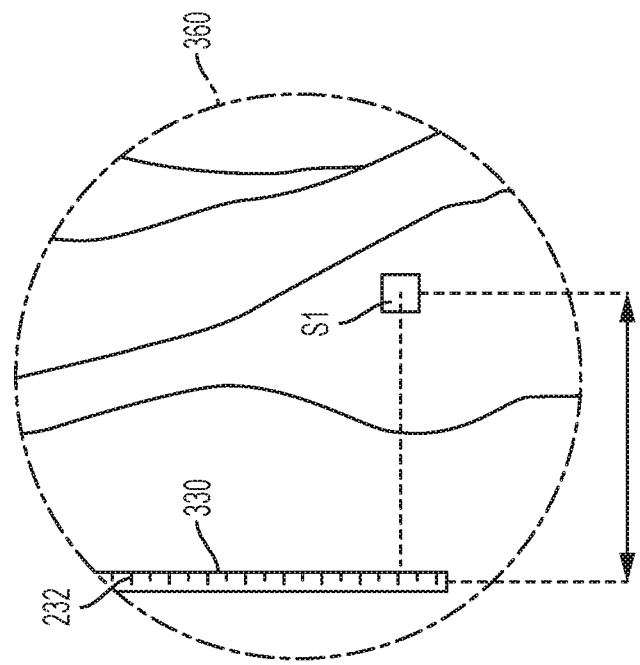
FIGS. 3A-B illustrate a portion of an image illustrating the cervical anatomy (FIG. 3A) and the sacral anatomy (FIG. 3B) with the displacement measured.
Figure 3A:
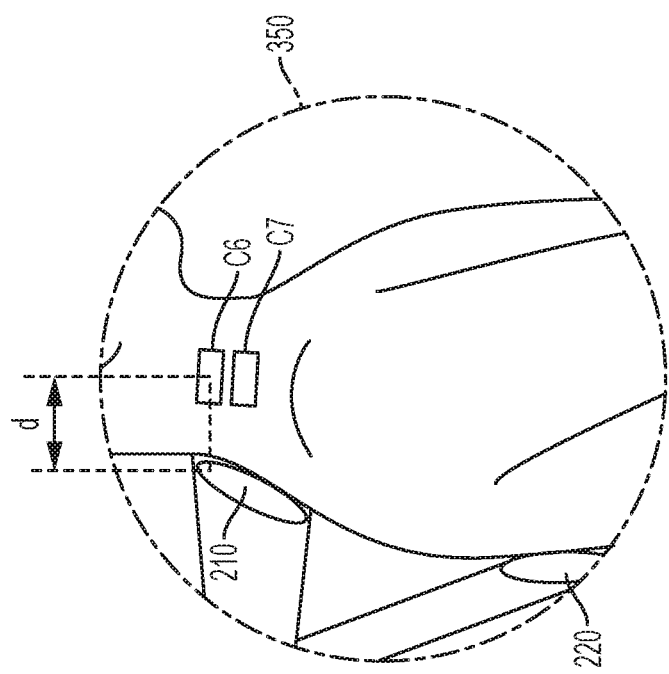

FIGS. 3A-B illustrate a portion of the resulting image of the cervical anatomy (FIG. 3A) and the sacral anatomy (FIG. 3B) with the displacement measured resulting from using the device in FIGS. 2A-B. Portions of the fiducial plumb line device 200 (first radiopaque arm 210, and second radiopaque arm 220) are visible within the imaging field of view 350 in FIG. 3A as well as the cervical anatomy C6 and C7. The displacement d between the cervical plumb line and the cervical anatomy can be measured from the image. As shown in FIG. 3B, the position of the S1 vertebra can also be detected using the reference markings 232 on the third radiopaque arm 330 in an extended mode.

As shown in FIGS. 2A-B, the cervical plumb line device has three main components: A fiducial and patient-mounting member (the first radiopaque arm 210 can also include a fiducial marker), a plumb line member (the third radiopaque arm 230), and a connecting arm scaling member (the second radiopaque arm 220).

The fiducial plumb line device 200 can provide a fiducial marker that appears in the image of the patient that is taken for reference. The fiducial plumb line device 200 is, for example, a shoulder or neck mounted component that is puts a radiopaque fiducial marker in a fluoroscopic lateral image of, for example, the C6 or C7 cervical region of the spine, such that the distance between the C6 or C7 vertebra and the fiducial marker can be calculated. As will be appreciated by those skilled in the art, the fiducial marker can be a ball or some other object mounted on a connecting arm to a patient facing mounting mechanism that includes pads, bolsters, straps, and other mechanisms for physically positioning the fiducial marker fixedly with respect to the patient such that the relative distance between the fiducial marker and, for example, the C6 or C7 vertebra cannot change while the cervical plumb line member is mounted, and such that the connecting arm is positioned as close to perpendicular in the coronal plane as possible (so that length distortion in the sagittal plane is minimized). The fiducial marker could serve as a ball joint for the plumb line device.

The plumb line device can have a variable length metal (or radiopaque) arm that hangs rotatably from the fiducial marker as illustrated in FIGS. 2A-B. The plum line device for example could be a telescoping metal member, such as a ruler, or some other object of variable length. In operation, the plumb line can be disconnectable from the fiducial patient mounting. The plumb line member can have radiopaque length markers, so that the length of the fiducial can be read in the resulting lateral view fluoro images. Additionally, the plumb line member can be weighted at the end opposite the connection end to facilitate orienting the plumb member so that it is perpendicular to the floor. The plumb line member can rotate about a connection point to swing freely and align itself to the direction of gravity (i.e., perpendicular to the floor).

The third aspect of the cervical plumb line device is the connecting arm scaling object. The connecting arm is a scaling object of a fixed linear dimension that, when viewed radiographically, can be calibrated to account for out-of-plane affects that can add length distortion to sagittal plane distance measurements taken from the fluorographic image. This scaling object may be linear only, or may be bi-linear, where it is comprised of orthogonal line segments that would be visible in lateral images.

In operation of the cervical plumb line device, there is typically a three step process:

(1) mount the cervical plumb line device and take a first seated cervical image of the patient with the cervical plumb line device (the vertical plumb-line member may be in either a retracted or extended position), (2) stand the patient up, and adjust the length of the plumb line until it freely hangs and is visible in a field of view in which it is also possible to image the posterior edge of the sacrum and take a second image, then (3) perform image processing on the first and second images. The imagine processing would include: (3a) in the first image, markup of the four corners of the lateral projection of C6, C7, or any other vertebral body of interest, then measure the exact displacement between the back of the relevant anatomy (e.g. C6 and C7) and the fiducial object and point of origin for the plumb line; (3b) use of the second image to measure the exact displacement between the back of the sacrum and the plumb line; and (3c) combine these two images to create a reconstructed by reading the length of the telescoping member and by aligning the plumb lines across both images to derive the relevant SVA measurements.

Use of a Patient Handling Device and Analytic Methods to Estimate a Degree of Pelvic Anteversion and Retroversion Another aspect of the disclosure relates to the use of a patient handling device to achieve a measurement of pelvic ante-retroversion.

Figure 4C:
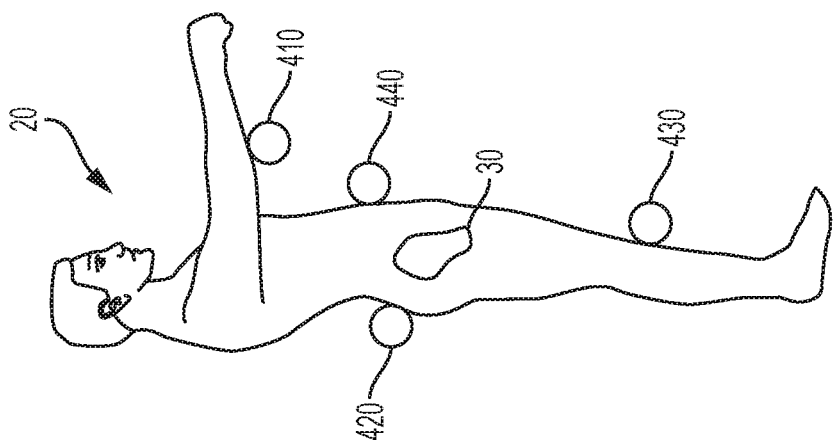
FIGS. 4A-C illustrate a patient in a normal upright position (FIG. 4A), a bent knee upright standing position (FIG. 4B), and a spinal extension upright standing position (FIG. 4C) with the bolster connection points.
Figure 4B:
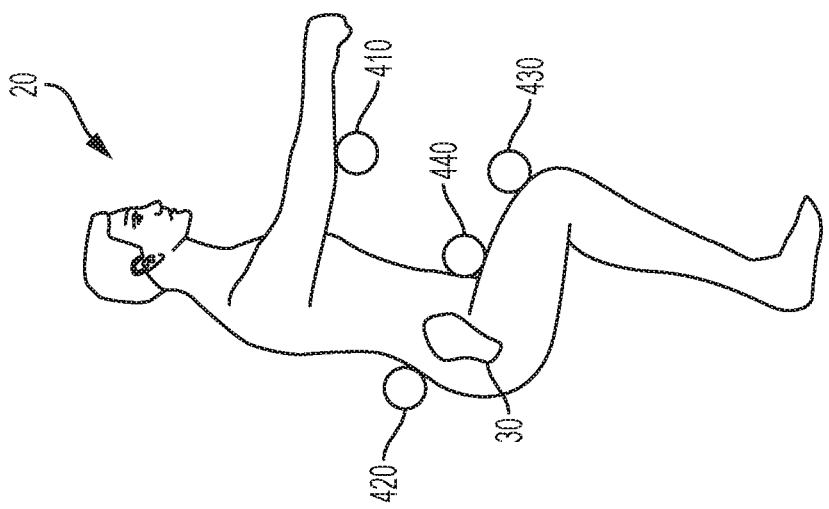
Figure 4A:
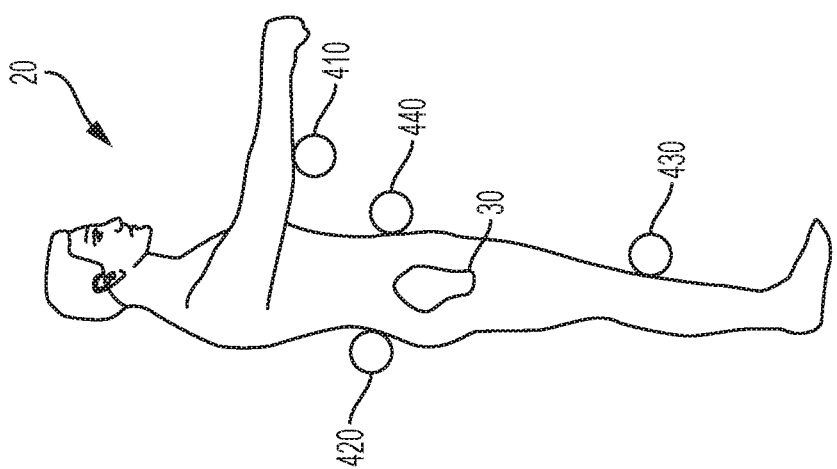

FIGS. 4A-C illustrate a patient 20 in a normal upright position (FIG. 4A), a bent knee upright standing position (FIG. 4B), and a spinal extension upright standing position (FIG. 4C) with the bolster connection points. A first connection point 410 is positioned for the patient 20 to engage ventrally with their arms or hands. A second connection point 420 is positioned to engage the patient 20 dorsally at the sacral curve of the spine. A third connection point 430 engages the patient 20 ventrally above the knee. A fourth connection point 440 engages the patient 20 ventrally at the hips. For reference the hip bone 30 is illustrated. The patient handling devices of FIGS. 4A-C are used to assure a known controlled amount of knee or hip flexion by the patient. The patient handling devices also facilitate achieving a target posture, with assistance and pelvic bolstering by the patient handling device. The target posture approximates what the patient would strive to achieve without assistance. One skilled in the art would appreciate that there could be numerous combinations of these four types of bolsters, including configurations wherein only one, two, or three of the four bolsters illustrated are required. Additionally, a plumb line device, such as described in FIGS. 2A-B, could be mounted to the patient's hip, adjusted in its sagittal depth, to provide an indicator of an optimal position of the pelvis relative to the ankles and knees of the patient. A plumb line device could also be positioned to assure that the knee and ankle are optimally aligned. Positioning a plumb line device in any of these positions would have the effect of allowing for precise motion of the pelvis relative to the knees and ankles to achieve a physiologically optimized plumb line. In some configurations, the plumb line can also be a simple radiographic marker.

Patient bolsters could be used, such as bars and handles illustrated in FIGS. 4A-C, to allow the patient to support themselves in a full neutral upright posture. The bolsters could additionally have other mechanisms to achieve a specific level of anteversion or retroversion of the hips. Any number of bolstering schemes could be provided, but generally the one that is preferred is the one that would be the "base" of a balanced spine. For this purpose-determining the ideal angle of pelvic tilt in a corrected spine, in certain therapies (see WO2015/040552 A1 and WO2015/056131 A1) there is typically a manual correction to pelvic tilt to account for post-operative decompensation, with such manual corrections being used to project a post-operative pelvic tilt, which in turn can be used to project any number of post-operative sagittal alignment measurements.

In use, the patient could be imaged in an uncontrolled manner at a first time, and in a controlled manner using the bolster device of FIG. 4 at a second time—either before or after the first time. A plumb line indicator device, such as shown in FIGS. 2A-B, can also be used within the field of view of each of the images at the target location. Alternatively, the plumb line could be secured directly from the imaging equipment (if, for example, the modality incorporates a millimeter calibration functionality After the desired images are acquired, an expected lordosis can be determined and a sagittal alignment correction can be added. The expected lordosis and sagittal alignment correction could be projected such that a post-operative lordosis and correction could result in a set of sagittal alignment measurements that more closely approximate ranges observed in asymptomatic subjects.

The correction factor can be used to project a post-operative sagittal alignment for a spine surgery patient. In constructing the SVA, the pelvic tilt can be set to a value measured from the apparatus, then the corrected spine is "connected" to the sacrum, then the SVA targets can be made to determine overall correction targets.

Other mechanisms for determining overall correction targets also include the incorporation of automated diagnostics that detect and measure vertebral wedge fractures. Correction targets could be added to, for example for any fracture that occurs before the inflection point between lordosis and kyphosis (the thoracic apex) into lumbar correction goals, and also into kyphosis goals for the spine segment superior of the thoracic apex.

Figure 5:
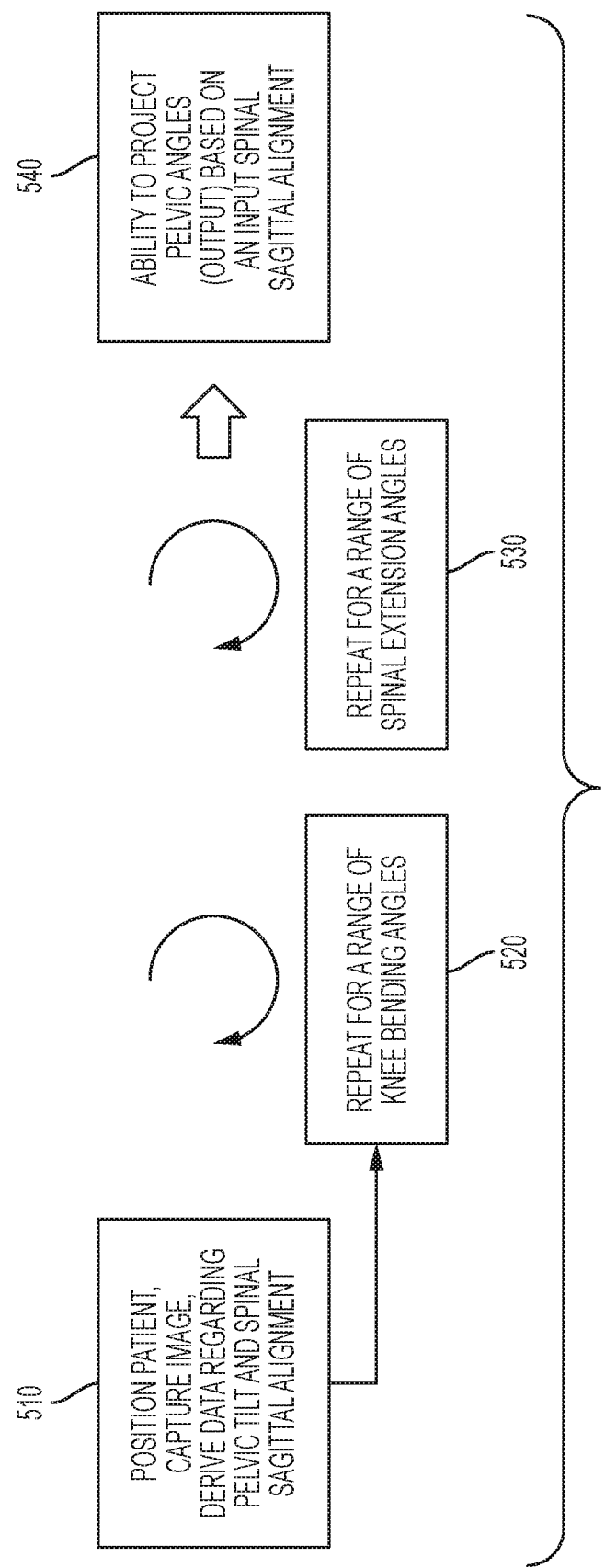
FIG. 5 is a flow diagram illustrating steps for positioning a patient, performing a range of knee bending and spinal extension angles which results in projected pelvic angles.

As shown in FIG. 5, the patient is positioned, an image is captured, and data is derived regarding pelvic tilt and spinal sagittal alignment 510. This process can be repeated for a range of knee bending angles 520. Additionally, or in the alternative the process can be repeated for a range of spinal extension angles 530. The output of the process provides the ability to project pelvic angles as an output based on an input spinal sagittal alignment 540.

Specialized Trialing Instrument for Use in the Implantation of Spinal Interbody Devices.

Also disclosed is a trial instrument, usable in spine fusion surgery. The trial instrument is illustrated in FIGS. 6 and 7A-D. This trial instrument 600 has a proximal user-end 620, and a distal implant end. The trial instrument 600 has a shaft 622 which has the proximal user-end 620 at one end (e.g., handle) and the tool at the other end. As will be appreciated by those skilled in the art, there will be different configurations of the trial instrument for lateral, oblique, and posterior-lateral, and trans-foramina interbody fusion procedures. Using the trial instrument can minimize tissue disruption to the end plates of the vertebral bodies and improve surgical work flow. For example, when the distal end of the trial instrument is closed it can have a width of about 8 mm, when it is opened it can have a width of about 16 mm. Using the trial instrument avoids disrupting the vertebral endplates multiple times.

The distal end of the trial instrument 600 has two distracting plates 630, which are shown perpendicular to one another, to which can be applied a controlled and measurable distracting force. The distracting plates 630 are moveable with respect to the shaft 622 and are connected via an arm 640 and a hinge 650. On the proximal user end, is the ability to control the applied force and/or displacement, by use of a controller 610. A suitable controller 610 includes, for example, a rotating knob which "clicks" when a pre-specified torque or force is achieved at the distal end between the distracting plates. Alternatively, a strain gauge can be provided to allow the surgical user to see the total displacement between the distracting plates 630. Measurements of force and/or displacement (from the gauges) could additionally be shown physically via a gauge that is radiopaque and readable via the radiographic image in some configuration. One skilled in the art would also appreciate that the displacement and/or force measurements could be transmitted via electronic sensors and communicated via suitable wired or wireless electronics.

Figure 7A:
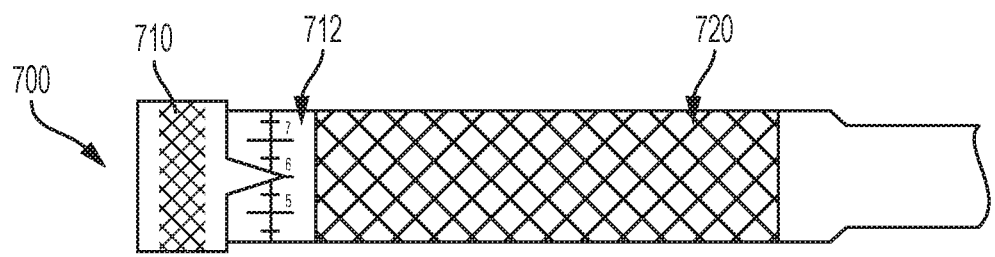
FIGS. 7A-D illustrates additional details and variations of the trial instrument of FIG. 6.
Figure 7B:
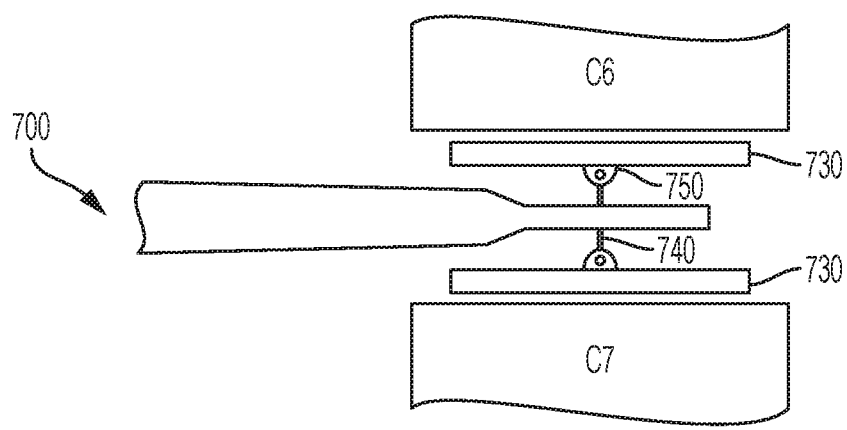

FIG. 7A is a close-up of the proximal end of the trial instrument 700 showing the rotatable knob and which has a pointer to illustrate the force applied at the distal end. The controller 710 can include reference markings 712 to provide the surgical user feedback to the amount of force applied and/or the amount of displacement between the plates 730. The handle 720 can have surface treatment, as illustrated, to ensure the surgical user has a solid grip. The handle 720 can be cylindrical, as shown, or can have wells on a surface to correspond to a surgical user's finger placement. The handle 720 is positioned at a proximal end of an elongated shaft 722. FIG. 7B is a close-up of the distal end of the trial instrument 700, where the trial instrument is positioned between two end plates of vertebral bodies C6 and C7. The distracting end plates 730 engage the trial instrument via rotatable arms 740 which have a hinged rotation point 750. The distracting end plates 730 can remain parallel to one another during use or can be non-parallel.

Figure 7D:
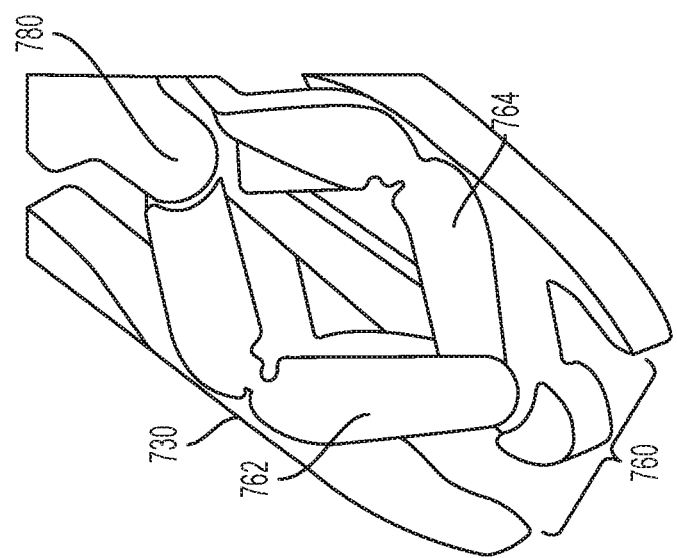
Figure 7C:
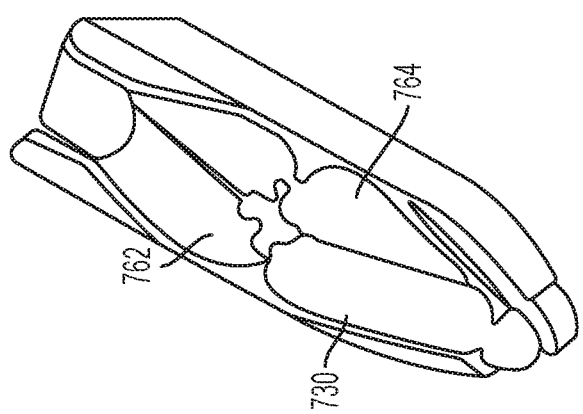

The distal end configuration illustrated in FIGS. 7C-D, illustrates distracting end plates 730 that are positioned at the distal end of the elongated shaft 722. The distracting end plates 730 are controllable by a mechanism that allows for a controlled displacement between the plates, such as a scissor jack mechanism 760 or scissor lift. The scissor jack mechanism 760 is a pantograph which is a mechanical linkage connected in a manner based on parallelograms. The scissor jack mechanism 760 creates a foldable support that has a plurality of members 762, 764 which are rotatable about a rotation point 780 and which form a cross-crossed pattern when viewed from the side. The scissor jack mechanism 760 functions like a spring where the elevation or displacing motion of the two distracting end plates 730 takes place due to the application of pressure by the surgical user at the proximal handle. One skilled in the art would recognize that any number of other mechanical distraction mechanisms could be adopted to accomplish a controlled and/or measured displacement of the plates 730 without departing from the scope of the disclosure.

In use, the endplate facing surface of the distal end of the trial instrument can pivot freely about the rotation point and assume a range of angles so that the trial instrument can assume the angle between the endplates. The use of the trial instrument 700 facilitates avoiding posterior osteotomies, ALL releases and ALL resections. Additionally, use of the trial instrument avoids unnecessary distraction and/or resection of the anterior and posterior ligaments. Use of the trial instrument avoids distracting the PLL during insertion of posterior devices and can precisely control the amount of ALL stretching, adding only the amount required and avoiding over-stretching. Use of the trial instrument also avoid stress loading on the endplates of the vertebral bodies of the spinal level and the potential resulting destruction of cortical tissue caused by subsidence (which can occur when implants are used that have undersized PDH). Additionally, use of the device avoids errors in pedicle screw placement when surgical navigation/robotics are used. Moreover, distraction and compression of the spinal level via posterior instrumentation can be avoided unless necessary. As will be appreciated by those skilled in the art, a properly fitted fusion device should not require posterior adjustments.

When used for anterior distraction, the trial instrument avoids disrupting the posterior side. This is because posterior targets are based on how low, not how high, the posterior side can go. Distraction or compression, if required, can be added when adding posterior instrumentation. The trial instrument also has a gauge which can report ADH, then, in the case that an intra-operative confirmation system is being used, the capture/register can be skipped and the ADH can simply be manually input into the system. This allows all key parameters to be calculated while avoiding the capture/register workflow that would otherwise be required if the instrument were used in combination with an intra-operative confirmation system.

The trial instrument allows the surgical user to start with a minimum level of tissue disruption, and then assess intraoperative % TCA, °PI–LL and MID to determine if further disruption is required. The surgical user starts with a minimum level of ALL and PLL disruption. A determination of the minimum ALL tension is made, then the interbody is expanded to a minimum ALL tension. Posterior instrumentation, set screws, and rods are positioned but not locked. One or more intraoperative confirmations is performed, e.g., by obtaining a fluorographic shot at four point registration to determine % TCA, °PI–LL, MID and MLO. From there a decision is made as to whether the minimum disruption was enough, if not then further distraction, compression or reduction is made followed by an updated confirmation.

Distraction using the trial instrument achieves the following: (1) it allows for distraction of the anterior side of the vertebral disc space only, (2) it has a variable displacement mechanism, such as a scissor jack shown in FIG. 7C-D, to provide a controlled displacement between the anterior side of a vertebral endplate, (3) the distraction plates are mountable via a mechanism that lets the distraction plates assume any angle relative to each other, so that there is maximum contact between the vertebral body endplates and the distraction plates; and (4) the distraction plates can be radio opaque, while other components of the trial instrument are radiolucent.

The trial instrument output can be used to input directly into an intra-operative navigation system, for the purpose of providing the surgical user specific instructions and surgical parameters, such as what size and type of interbody device to select, or how much further adjustment needs to be done to the fusion construct to achieve the target geometry.

By connecting the trial instrument directly to an intra-operative navigation system, the trial instrument can be used to provide a direct data link via a wireless or wire based connection. The trial could provide the information to the computer to measure the specific force-displacement curve for a patient's ALL (in other embodiments, it could be directed at measuring the PLL and the device as a whole could be adapted for this purpose). Knowing this force, it would be possible to determine a projected maximum range, possibly by looking up reference data taken from in vitro experimentation. There could be other features enabled by having this data to support a more minimally invasive approach to fusion surgery, such as linking the instrument to information systems that can provide optimal configuration parameters (in terms of force and/or displacement measurements, interbody device sizes, interbody device selection, and the selection, sizing, configuration, and other parameters related to the implantation of posterior instrumentation during spinal fusion surgery). Having a torque-controlled or force controlled mechanism could allow the intra-operative system to determine the ideal amount of force, possibly by consulting information about the patient's bone density, demonstrated range of motion at that level, and/or data from in vitro studies, and then have the instrument automatically set to allow only up to the specified level of distracting force.

Figure 8:
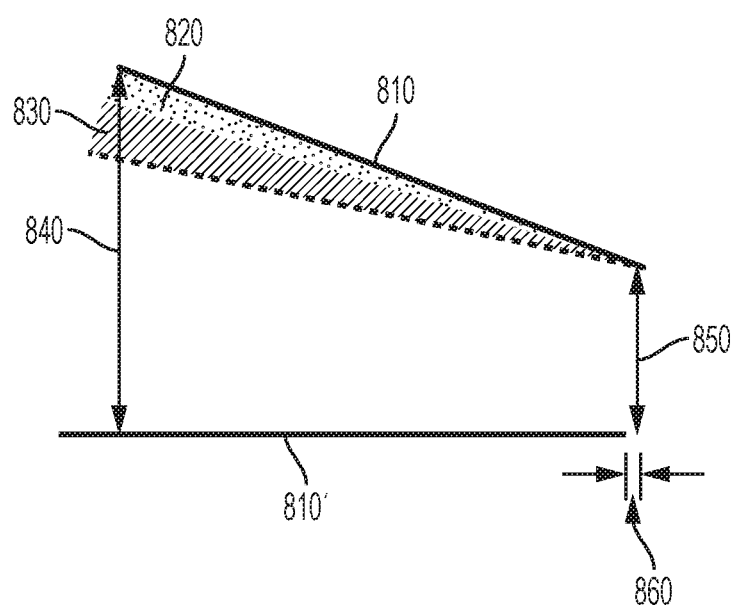
FIG. 8 illustrates geometric boundaries for a patient.

As shown in FIG. 8, two vertebral end plates are shown 810, 810'. The space between the end plates is where an intervertebral disc (or intervertebral microcartilage) is positioned. Disc height, expected lordosis, and listhetic offset can be derived from neighboring vertebral levels. A target construct can be automatically rendered by the system for each 1-level and 2-level fusion scenarios. The height at the left side 840 from upper end plate 810 to lower end plate 810' can be, for example, 23.5 mm, while the height at the right side 850 can be 10.1 mm. A 1.1 mm distance 860 between an edge of the upper end plate 810 and an edge of the lower end plate 810'. A post-operative kyphosis margin 820 can be determined, along with a sagittal alignment correction 830. The post-operative kyphosis margin 820 can be, for example, 4°, and the sagittal alignment correction

830 can be, for example, 5°. In this scenario, the overall expected segmental lordosis is about 12°. The expected lordosis can be set based on user-selected distribution function. A sagittal alignment correction can be added in the difference between PI–LL and +/−10.

Figure 9:
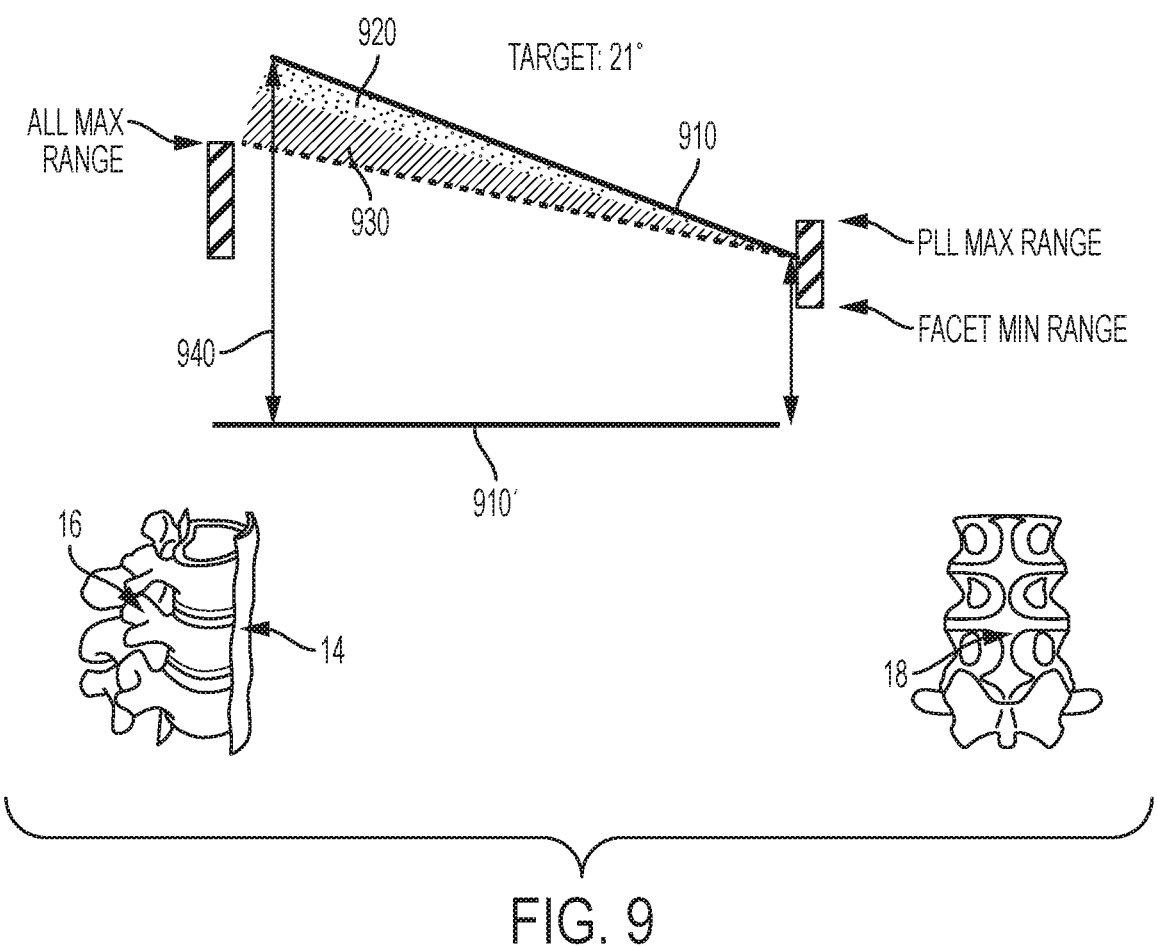
FIG. 9 illustrates patient specific geometric boundaries for a fusion construct that incorporates safe and non-injurious operating ranges for the ALL, PLL and facets.

FIG. 9 illustrates safe dimensions that are patient-specific boundaries for a fusion construct that represents safe and non-injurious operating ranges for the ALL, PLL and facets based on two vertebral end plates are shown 910, 910' in an image. For reference the facets 16 and anterior longitudinal ligament 14 is shown, along with the posterior longitudinal ligament 18. The target illustrated in FIG. 9 is 21°, and the $ALL_{max}$ range is shown in the left side, while the $PLL_{max}$ range and $Facet_{min}$ ranges are shown on the right. Overlaying known safe data onto the target construct allows the surgical user to know if and how much disruption of the vertebral endplates is required. The post-operative kyphosis margin 920 can be determined, along with a sagittal alignment correction 930.

The % TCA, or percent target construct achievable (TCA), distills the decision-making process down to a number that can assist the surgical user in managing difficult trade off decisions. For any given fusion construct, % TCA is the percentage that the construct achieves the target lordosis values.

$$\% \text{ TCA} = [\text{Lordosis}_{Current}]/[\text{Lordosis}_{Target}] \quad \text{(EQ. 1)}$$

The pelvic incidence minus the lumbar lordosis measurement for the construction is the PI–LL. The % TCA and PI–LL analysis provides an assessment of the trade-off between the future re-operation risk (ALD risk) vs. the risk of more tissue disruption during the current procedure, both pre-operatively and intra-operatively. For example, the most minimally invasive approach achieves a 65% TCA and 13° PI–LL. From these numbers, the surgical user can determine whether this is enough correction for the patient, or whether more disruptive options are preferable to achieve greater correction. Will this patient be able to toleration a re-operation in 5-15 years? Is the patient likely to be too old or too infirm for another operation? What type of pain did the patient complain of? What matters most to the patient—minimal disruption or minimal risk of re-operation?

The millimeters of direct compression (MID) represents that the size of the increase in posterior disc height (PDH) above the minimum value observed during the functional testing. MLO is the millimeters of listhetic offset. A given fusion construct can be characterized by the following:

$$\text{MID} = [\text{PDH}_{Current}] - [\text{PDH}_{Min}] \quad \text{(Eq. 2)}$$

$$\text{MLO} = [\text{Offset}_{Current}] \quad \text{(Eq. 3)}$$

Comparing the percentage of TCA and the MID enables an assessment of the trade-off between the future re-operation risk (ALD risk) versus the competing goal of achieving the desired level of indirect decompression. MLO measurements are useful in finalizing the pedicle screw depth and/or screw-rod connections.

Including PDH targets when sizing implants maximizes the surface area of the implant/vertebral endplate interface to maximize arthrodesis (e.g., surgical immobilization of the adjacent vertebral bodies by bony ingrowth). Additionally, selection of devices can be optimized to avoid compromised ingrowth due to the reduced ingrowth surface area. The use of non-expandable devices can be preferred over expandable devices to avoid such compromised ingrowth. Controlling the amount of post-operative tension on the ALL by determining optimal tension pre-operatively or operatively can assure sufficient compression to promote arthrodesis while avoiding over-distraction between the vertebral bodies. Additionally, minimized disruption of the endplates through repetitive or high-force trailing preserves a maximum amount of healthy tissue to promote ingrowth.

Indirect decompression increases posterior disc height which reduces segmental lordosis. Indirect decompression is often a primary objective in degenerative fusion. Achieving an indirect compression, however, can be achieved at the expense of lordosis—assuming the ALL remains intact. Consequently, surgeons balance lordosis targets against posterior disc height targets.

TABLE 1

Pre-Operative Decision Support

| | Scenario 1: Maximum Lordosis | Scenario 2: Patient Average PDH | Scenario 3: Maximum Indirect Decompression |
|---|---|---|---|
| Lordosis Possible | 16° | 11° | 8° |
| Target Lordosis | 21° | 21° | 21° |
| % TCA | 77% (16/21) | 54% (11/21) | 36% (8/21) |
| °PI - LL | 13° | 16° | 19° |
| MID | 0 mm | +3.2 mm | +5.5 mm |

Table 1 provides an example where % TCA, PI–LL and MID are assessed against each other in selecting a surgical approach. Based on the results in the example, a decision process can be performed as follows:

If the % TCA is too low and the PI–LL are too high, consider a 2 vs. 1 level fusion; consider posterior osteotomy; consider anterior release.

If the % TCA is high enough and PI–LL is low enough, no need to consider a more aggressive surgical plan. In this scenario, if lordosis is the priority, select maximum lordosis scenario (77% TCA). If decompression if the priority, select the maximum indirect decompression scenario (36% TCA) and +5.5 MID.

Figure 10:
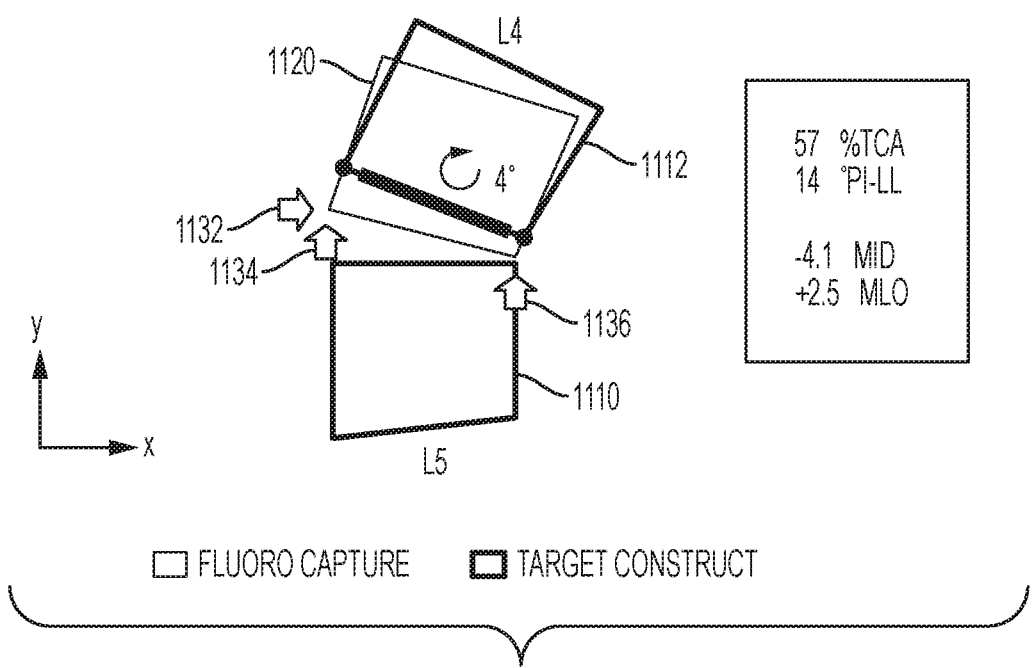
FIG. 10 illustrates current fluoro capture vs. target construct established for the patient.

FIG. 10 illustrates a fluoro capture versus a target construct. Two vertebra, L4/L5 are illustrated as an example. The fluoro capture 1120 of L4, is offset from the target construct 1112 of L4 relative to the target construct 1110 of L5. The target construct 1112 of L4 has an offset 1130 of 4° to the position of the fluoro capture 1120. The degree of offset 1130 is also reflected in a mechanical shift of the position of the vertebral facing end plates. The L5 endplate 1114 should rotate 4° from the captured L4 endplate 1116, to target L4 endplate 1115. This is achieved with a shift along the x-axis of −1.4 mm, a shift on the y-axis at a first position of the x-axis 1134 of 15.2 mm and a shift on the y-axis at a second position of the x-axis 1136 of 4.1 mm.

The process for analyzing lateral and oblique devices intraoperatively includes, determining and identifying which spinal levels are to be modified, where each spinal level is a pair of vertebral bodies. So, for example, spinal level 1 could be L4/L5 and spinal level 2 could be L5/S1. Next the surgical user accesses and prepares the disc space between the facing end plates of each selected spinal level and inserts the trial device of FIGS. 2, 6 and 7. The trial device measures ADH and, for example, anterior distraction (for lateral/oblique impacted devices), the distance between the facing end plates of the vertebral bodies of the selected spinal level can be expanded as desired. The trial device can be distracted to achieve a desired tension. Data can be captured and registered for a tension to produce a percentage lordosis target achieved, specify an optimal implant based on the target PDH and ADH as measured by using the trial device. The process of distracting the vertebral bodies of the spinal level and capturing and analyzing data can be repeated and iterated as necessary to optimize the results achieved. This provides essentially real-time iteration and optimization of the sizing process to ensure the best results are achieved after surgery. Once the distraction, capture, registering, and data analysis steps are completed, and a device is selected the selected device is implanted. Following implantation, additional capturing and registering of data and adjusting of the construct with posterior instrumentation can be performed. This post-implantation process looks at the percent lordosis target achieved and the amount of offset of the target. Navigation and robotics can be used for pedicle screw placement. The workflow for lateral, oblique and posterior intra-operative and post-operative is largely the same. The pre-operative decisions are different based on the drivers that depend on the surgical approach to be taken.

The process for analyzing ADH and PDH adjustable devices intraoperatively includes, determining and identifying which spinal levels are to be modified, where each spinal level is a pair of vertebral bodies. So, for example, spinal level 1 could be L4/L5 and spinal level 2 could be L5/S1. Thereafter, the expandable implant is inserted. The posterior side of the device is expanded to the target mm for the PDH. For this step, implants with independent ADH and PDH adjustability plus instruments that can achieve a specific posterior displacement in mm is optimal. The anterior side of the device is expanded to a minimum target for ALL tension. At this point, determination of how close the spacing between the endplates of the vertebral bodies of the spinal level is to the target extraction is determined. Once the device is implanted and the height is adjusted, the results are captured and registered and a determination of percentage of lordosis to the target has been achieved, and the overall offset to the target. Anterior and/or posterior expansion adjustments can be made as needed. Additional adjustments of the construct with the posterior instrumentation can also be made. The workflow for lateral, oblique and posterior intra-operative and post-operative is largely the same.

In all of the above steps, the computer would be instrumental in assessing a current captured and registered vertebral body geometry to that of the target. This involves the application of complex geometric formulae to the relative position data from the capture/register process to derive easy-to-use measurements of the additional geometric adjustments to the fusion construct required to achieve the target geometric configuration. These complex geometric formulae include: (1) comparing four point templates for vertebral body endplates associated with a target geometric configuration to the four point templates for vertebral body endplates as taken from a "capture/register" process executed by an intra-operative surgical execution system, (2) based on this comparison, generating specific instructions as to the amount of rotation, anterior disc height, posterior disc height, or listhetic offset that would need to be added to the fusion construct to achieve the target. The geometric formulae that are used would compare the superior edge of the inferior vertebral body of a spinal level to the inferior edge of the superior vertebral body of the level, and derives measurements of angulation (lordosis), ADH, PDH, and listhetic offset of the level from the "capture/register" process, then calculates the differences relative to a target configuration. Instructions to the user in terms of additional geometric changes to make could be expressed in terms of additional lordosis, ADH, PDH, and/or listhetic offset to add to the fusion construct.

As an example of the complex geometric formula, assume that $P1(x,y)_{Ant/Sup}$, $P1(x,y)_{Post/Sup}$, $P1(x,y)_{Ant/Inf}$, and $P1(x,y)_{Post/Inf}$ refers to the four corner points of a first vertebral body template (the subscripts denote which corner point, anterior superior, posterior superior, anterior inferior, and anterior superior, respectively). Further assume that $P2(x,y)_{Ant/Sup}$, $P2(x,y)_{Post/Sup}$, $P2(x,y)_{Ant/Inf}$, and $P2(x,y)_{Post/Inf}$ refers to the four corner points of a second vertebral body template. If the first template corresponds to a target configuration, and the second template refers to the location of a capture/register process done intra-operatively, then the amount of additional lordosis required to achieve the target would be calculated by the formula:

$$2*\text{Arctangent } [(P2(x)_{Ant/Inf} - P1(x)_{Post/Inf})/(P2(y)_{Ant/Inf} - P1(y)_{Post/Inf})*0.5]$$

For any of the procedures, post-operative review can be performed at suitable intervals: e.g., 6 months, 9, months, 12 months, 18 months, 24 months, and so on. A detection of radiographic evidence of adjacent level disease (ALD) based on changes from pre-operative values can be detected. The radiographic evidence precedes clinical evidence and can be used for patient intervention. From the data, iteration and/or escalation of treatment can be recommended depending on the symptoms and the extent of the radiographic progression. Data and recommendations can be provided to the surgical user to manage ALD risk. Custom reports can be generated which focus on managing ALD risks, coupled with direct-to-patient disease management offerings with interventions to delay or avoid re-operation. Other recommendations, such as regenerative therapy, can also be made. Recommendations for additional testing or more frequent testing can be provided to allow for monitoring further progression based on post-operative data.

The systems and devices allow for assessing pre-operative risk of ALD and minimizing the ALD risk by adding lordotic corrections to the spine fusion constructs. Balancing of the lordosis correction goals can also be balanced against other surgical objectives and imperatives. Additionally, early ALD monitoring and detection is enabled. In some configurations, a direct-to-patient, disease management system can be used to empower patients with recommendations to proactively avoid or delay ALD progression and re-operation. Recommendations include, for example, reducing activity, modifying activity, substituting activity, weight loss, physical therapy, exercise or chiropractic intervention focused on improving core and/or neck strength, and physical therapy, exercise or chiropractic intervention focused on improving pelvic anteversion or retroversion.

Figure 11:
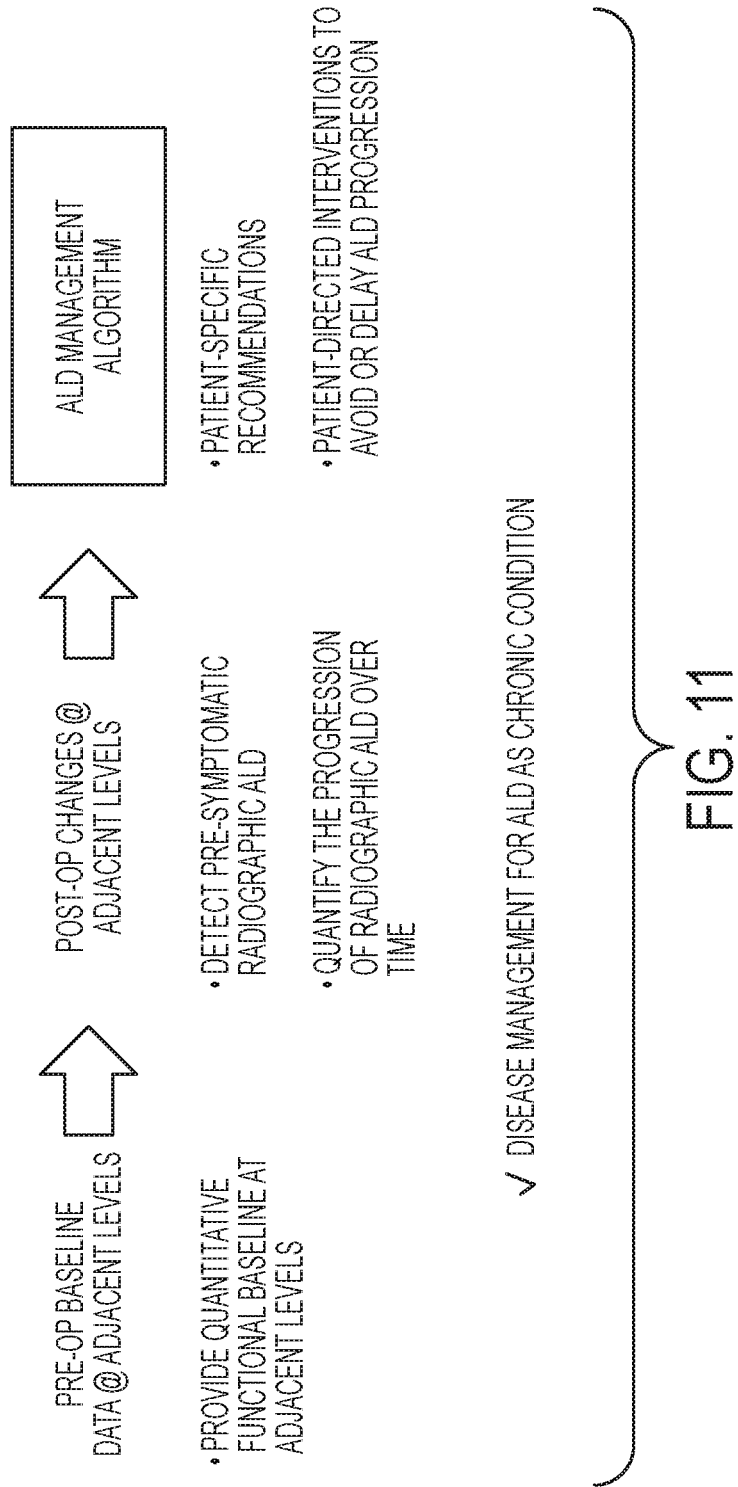
FIG. 11 is a flow diagram of processes for disease management.

FIG. 11 illustrates a process for disease management for ALD as a chronic condition. Preliminarily, pre-operative baseline data at adjacent levels is acquired. Acquiring pre-operative data at adjacent levels provides quantitative functional baseline information at adjacent levels which can be used to assess a variety of potential surgical processes. Post-operative changes at adjacent levels are also evaluated to detect pre-symptomatic radiographic ALD. This allows the progression of radiographic ALD to be quantified over time. Based on the pre-operative and post-operative information patient-specific recommendations can be made. Additionally, patient-directed interventions can be recommended to avoid or delay ALD progression.

The systems and methods according to aspects of the disclosed subject matter may utilize a variety of computer and computing systems, communications devices, networks and/or digital/logic devices for operation. Each may, in turn, be configurable to utilize a suitable computing device that can be manufactured with, loaded with and/or fetch from some storage device, and then execute, instructions that cause the computing device to perform a method according to aspects of the disclosed subject matter.

A computing device can include without limitation a mobile user device such as a mobile phone, a smart phone and a cellular phone, a personal digital assistant (PDA), such as an iPhone®, a tablet, a laptop and the like. In at least some configurations, a user can execute a browser application over a network, such as the Internet, to view and interact with digital content, such as screen displays. A display includes, for example, an interface that allows a visual presentation of data from a computing device. Access could be over or partially over other forms of computing and/or communications networks. A user may access a web browser, e.g., to provide access to applications and data and other content located on a website or a webpage of a website.

A suitable computing device may include a processor to perform logic and other computing operations, e.g., a stand-alone computer processing unit (CPU), or hard-wired logic as in a microcontroller, or a combination of both, and may execute instructions according to its operating system and the instructions to perform the steps of the method, or elements of the process. The user's computing device may be part of a network of computing devices and the methods of the disclosed subject matter may be performed by different computing devices associated with the network, perhaps in different physical locations, cooperating or otherwise interacting to perform a disclosed method. For example, a user's portable computing device may run an app alone or in conjunction with a remote computing device, such as a server on the Internet. For purposes of the present application, the term "computing device" includes any and all of the above discussed logic circuitry, communications devices and digital processing capabilities or combinations of these.

Certain embodiments of the disclosed subject matter may be described for illustrative purposes as steps of a method that may be executed on a computing device executing software, and illustrated, by way of example only, as a block diagram of a process flow. Such may also be considered as a software flow chart. Such block diagrams and like operational illustrations of a method performed or the operation of a computing device and any combination of blocks in a block diagram, can illustrate, as examples, software program code/instructions that can be provided to the computing device or at least abbreviated statements of the functionalities and operations performed by the computing device in executing the instructions. Some possible alternate implementation may involve the function, functionalities and operations noted in the blocks of a block diagram occurring out of the order noted in the block diagram, including occurring simultaneously or nearly so, or in another order or not occurring at all. Aspects of the disclosed subject matter may be implemented in parallel or seriatim in hardware, firmware, software or any combination(s) of these, co-located or remotely located, at least in part, from each other, e.g., in arrays or networks of computing devices, over interconnected networks, including the Internet, and the like.

The instructions may be stored on a suitable "machine readable medium" within a computing device or in communication with or otherwise accessible to the computing device. As used in the present application a machine readable medium is a tangible storage device and the instructions are stored in a non-transitory way. At the same time, during operation, the instructions may at sometimes be transitory, e.g., in transit from a remote storage device to a computing device over a communication link. However, when the machine readable medium is tangible and non-transitory, the instructions will be stored, for at least some period of time, in a memory storage device, such as a random access memory (RAM), read only memory (ROM), a magnetic or optical disc storage device, or the like, arrays and/or combinations of which may form a local cache memory, e.g., residing on a processor integrated circuit, a local main memory, e.g., housed within an enclosure for a processor of a computing device, a local electronic or disc hard drive, a remote storage location connected to a local server or a remote server access over a network, or the like. When so stored, the software will constitute a "machine readable medium," that is both tangible and stores the instructions in a non-transitory form. At a minimum, therefore, the machine readable medium storing instructions for execution on an associated computing device will be "tangible" and "non-transitory" at the time of execution of instructions by a processor of a computing device and when the instructions are being stored for subsequent access by a computing device.

Additionally, a communication system of the disclosure comprises: a sensor as disclosed; a server computer system; a measurement module on the server computer system for permitting the transmission of a measurement from a detection device over a network; at least one of an API (application program interface) engine connected to at least one of the detection device to create a message about the measurement and transmit the message over an API integrated network to a recipient having a predetermined recipient user name, an SMS (short message service) engine connected to at least one of the system for detecting physiological parameters and the detection device to create an SMS message about the measurement and transmit the SMS message over a network to a recipient device having a predetermined measurement recipient telephone number, and an email engine connected to at least one of the detection device to create an email message about the measurement and transmit the email message over the network to a recipient email having a predetermined recipient email address. Communications capabilities also include the capability to communicate and display relevant performance information to the user, and support both ANT+ and Bluetooth Smart wireless communications. A storing module on the server computer system for storing the measurement in a detection device server database can also be provided. In some system configurations, the detection device is connectable to the server computer system over at least one of a mobile phone network and an Internet network, and a browser on the measurement recipient electronic device is used to retrieve an interface on the server computer system. In still other configurations, the system further comprising: an interface on the server computer system, the interface being retrievable by an application on the mobile device. Additionally, the server computer system can be configured such that it is connectable over a cellular phone network to receive a response from the measurement recipient mobile device. The system can further comprise: a downloadable application residing on the measurement recipient mobile device, the downloadable application transmitting the response and a measurement recipient phone number ID over the cellular phone network to the server computer system, the server computer system utilizing the measurement recipient phone number ID to associate the response with the SMS measurement. Additionally, the system can be configured to comprise: a transmissions module that transmits the measurement over a network other than the cellular phone SMS network to a measurement recipient user computer system, in parallel with the measurement that is sent over the cellular phone SMS network.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

What is claimed is:

1. A system for producing geometric data describing an optimized spinal fusion geometric configuration at a spine level selected to receive spinal fusion, for use during spine surgery or during pre-operative planning, comprising a processor wherein the processor is configured to:
   (a) receive two or more non-overlapping images of a spine wherein the two or more images includes a cervical plumb line device,
      wherein the cervical plumb line device comprises
         (1) a first radiopaque arm having a first radiopaque arm first end and a second radiopaque arm end wherein the first radiopaque arm end is configured to engage a surface of a patient at a first location,
         (2) a variable length second radiopaque arm with a second radiopaque arm first end and a second radiopaque arm second end configured to engage a surface of the patient at a second location, wherein the second radiopaque arm rotatably extends from the first radiopaque arm, and
         (3) a third radiopaque arm having a connection end connected to the first radiopaque arm;
   (b) assess a current captured and registered vertebral body from the two or more non-overlapping images and a target vertebral body geometry;
   (c) compare a four point template for a vertebral body endplate taken from the captured and registered vertebral body from the two or more non-overlapping images to a four point template for a target geometry;
   (d) derive measurements of one or more of a spinal alignment and a range of motion at a spinal level selected to receive spinal fusion surgery from the two or more non-overlapping images; and
   (e) utilize the derived measurements to calculate an optimized spinal fusion geometric configuration for a target spine level; and
   (f) generate instructions for an amount of rotation, anterior disc height, posterior disc height or listhetic offset needed to achieve the optimized spinal fusion geometric configuration.

2. The system of claim 1 wherein the processor is configured to receive configuration parameters from a user.

3. The system of claim 1 wherein the processor is configured to analyze the calculated geometric configuration and recommending a surgical approach.

4. The system of claim 1 wherein the processor is configured to receive and process one or more of non-image patient data and additional images.

5. A system for producing geometric data describing an optimized spinal fusion geometric configuration at a spine level selected to receive spinal fusion, for use during spine surgery or during pre-operative planning, comprising a processor wherein the processor is configured to:
   (a) receive two or more non-overlapping images of a spine wherein the two or more images includes a portion of a cervical plumb line device, wherein the cervical plumb line device comprises one or more radiopaque arms;
   (b) assess a current captured and registered vertebral body from the two or more images and a target vertebral body geometry;
   (c) compare a four point template for a vertebral body endplate taken from the captured and registered vertebral body from the two or more images to a four point template for a target geometry;
   (d) process the received non-overlapping images to derive measurements of one or more of a spinal alignment and a range of motion at a spine level selected to receive spinal fusion surgery;
   (e) utilize the derived measurements to calculate an optimized spinal fusion geometric configuration for a target spine level; and
   (f) generate instructions for an amount of rotation, anterior disc height, posterior disc height or listhetic offset needed to achieve the optimized spinal fusion geometric configuration.

6. The system of claim 5 wherein the processor is configured to receive configuration parameters from a user.

7. The system of claim 5 wherein the processor is configured to analyze the calculated geometric configuration and recommending a surgical approach.

8. The system of claim 5 wherein the processor is configured to receive and process one or more of non-image patient data and additional images.

* * * * *